United States Patent [19]

Takaoka

[11] 3,940,064

[45] Feb. 24, 1976

[54] ATOMIZING EQUIPMENTS FOR ANESTHETIC LIQUID COMPOUNDS

[76] Inventor: Kentaro Takaoka, Avenida Bosque da Saude, 519, Sao Paulo, Brazil

[22] Filed: Feb. 10, 1975

[21] Appl. No.: 548,783

[30] Foreign Application Priority Data

Aug. 19, 1974 Brazil.................................... 6804

[52] U.S. Cl.................. 239/74; 239/338; 239/370; 128/194; 128/210
[51] Int. Cl.². ....................... B05B 7/26; B67D 5/38
[58] Field of Search ............ 239/338, 343, 370, 74; 128/194, 193, 209, 210; 222/28, 29, 48

[56] References Cited
UNITED STATES PATENTS

| | | | |
|---|---|---|---|
| 2,709,577 | 5/1955 | Pohndorf et al. ............... | 239/338 X |
| 2,882,026 | 4/1959 | Eichelman ..................... | 128/194 X |
| 3,018,777 | 1/1962 | Dietrich.......................... | 128/210 X |
| 3,077,307 | 2/1963 | Moore et al. ..................... | 239/338 |
| 3,353,536 | 11/1967 | Bird et al. ........................ | 128/194 |
| 3,733,060 | 5/1973 | Merritt............................. | 128/194 X |
| 3,826,255 | 7/1974 | Havstad et al. ................. | 239/338 X |
| 3,836,079 | 9/1974 | Huston............................. | 239/338 X |
| 3,874,379 | 4/1975 | Enfield et al. .................... | 128/194 |

FOREIGN PATENTS OR APPLICATIONS

| | | | |
|---|---|---|---|
| 1,011,397 | 4/1952 | France............................... | 239/338 |
| 1,244,281 | 9/1960 | France............................... | 239/338 |
| 247,325 | 5/1912 | Germany .......................... | 239/370 |
| 2,032,421 | 4/1972 | Germany .......................... | 128/194 |

*Primary Examiner*—Robert S. Ward, Jr.

[57] ABSTRACT

This invention relates to new vaporizers and particularly to atomizing equipment useful for dispensing anesthetic liquids.

8 Claims, 13 Drawing Figures

E-E

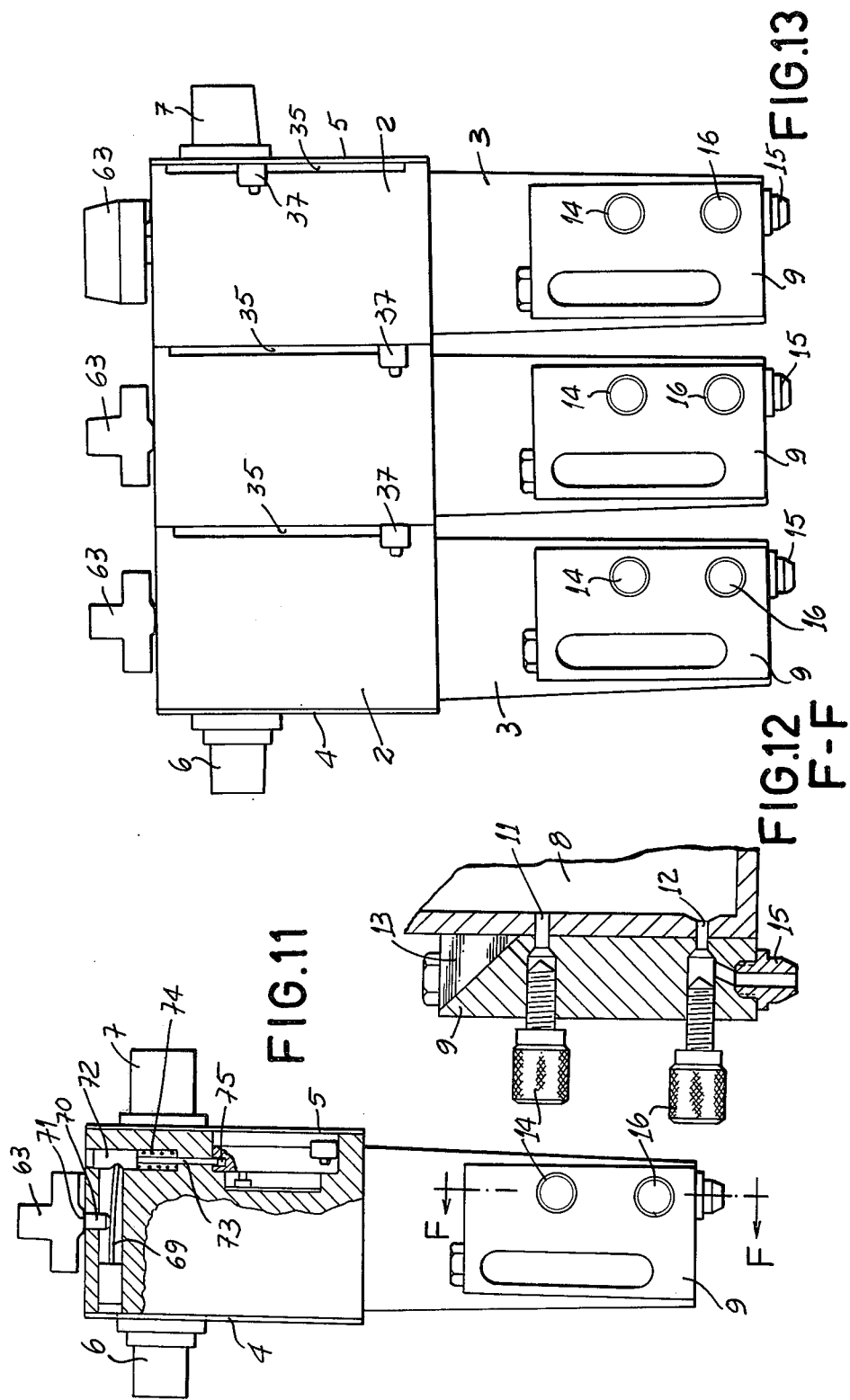

ATOMIZING EQUIPMENTS FOR ANESTHETIC LIQUID COMPOUNDS

BACKGROUND OF THE INVENTION

There are several liquid anesthetic vaporizers or atomizing devices presently used, all of them including an anesthetic liquid storage container, having a valve containing head, a lateral inlet for the atomizing gas and an opposite outlet for the gas supported active anesthetic composition.

In known devices, the gas carrier, usually oxygen, is bifurcated in two separate streams, the first one directly leading to the said outlet, without establishing a direct contact with the anesthetic liquid, and the second one being diverted to the vaporizing chamber where its saturation occurs before being united with a further mixture with the first stream to produce the final desired concentration. The ratio of the mixture of these streams is determined by the valves.

Several disadvantages have been encountered in the use of these conventional atomizing devices, such as the following:

the bulky body of the storage container, usually cylindrical, has prevented or made difficult the desired assembling of all the required parts, as well as the provision of a gang-unit;

another disadvantage in those devices having a gauged outlet, is grounded on the undesired influence of the variation of the inlet flow over the final concentration ratio by which the increase of the first will provoke a decreasing of the latter. The same influence is verified through the change of temperature, directly proportional to the increase of the said concentration, in spite of the use of bi-metal valves;

also, extreme care is required for the mounting of the needle valve which regulates the passage of the saturated stream from the storage tank to the upper head of the device, in order to ensure a perfect shut-off of the said passageway, and the operating knob of the valve does not immediately indicate the valve operating stage;

still another drawback of conventional atomizers for anesthetic liquid compounds is that there is no way to employ each and every kind of liquid composition with a single available device which results in the utilization of a plurality of different devices. This problem becomes particularly acute when a full battery or set of vaporizer units are assembled in a multiple or gang-unit device, each loaded with different kinds of anesthetic compounds.

Many other serious problems are faced by anesthetists all over the world due to the lack of reliability of suitable equipment. These problems have helped to render the anesthetic profession a highly specialized one.

DESCRIPTION OF THE INVENTION

It is a general purpose of this invention to improve vaporizing devices for anesthetic liquid compositions so as to remove all of the above-referred to disadvantages Illustrations of a preferred embodiment of the invention can be seen from the drawings in which:

FIG. 11 is a partial sectional view of the blocking mechanism of the needle valve;

FIG. 12 is a sectional view of the blocking mechanism, taken along the F—F line of FIG. 11; and FIG. 13 is a schematic front view of a gang-unit of vaporizers of FIG. 1.

Figure 1:
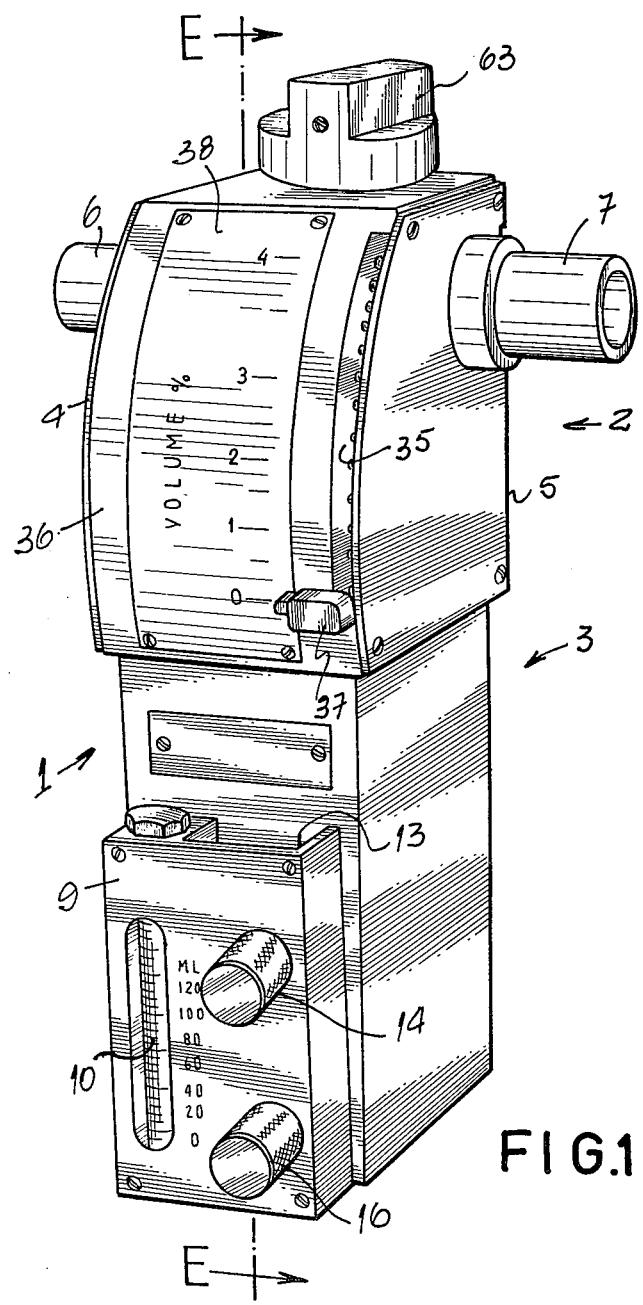
FIG. 1 is a perspective general view of an improved vaporizer made in accordance with this invention.
Figure 2:
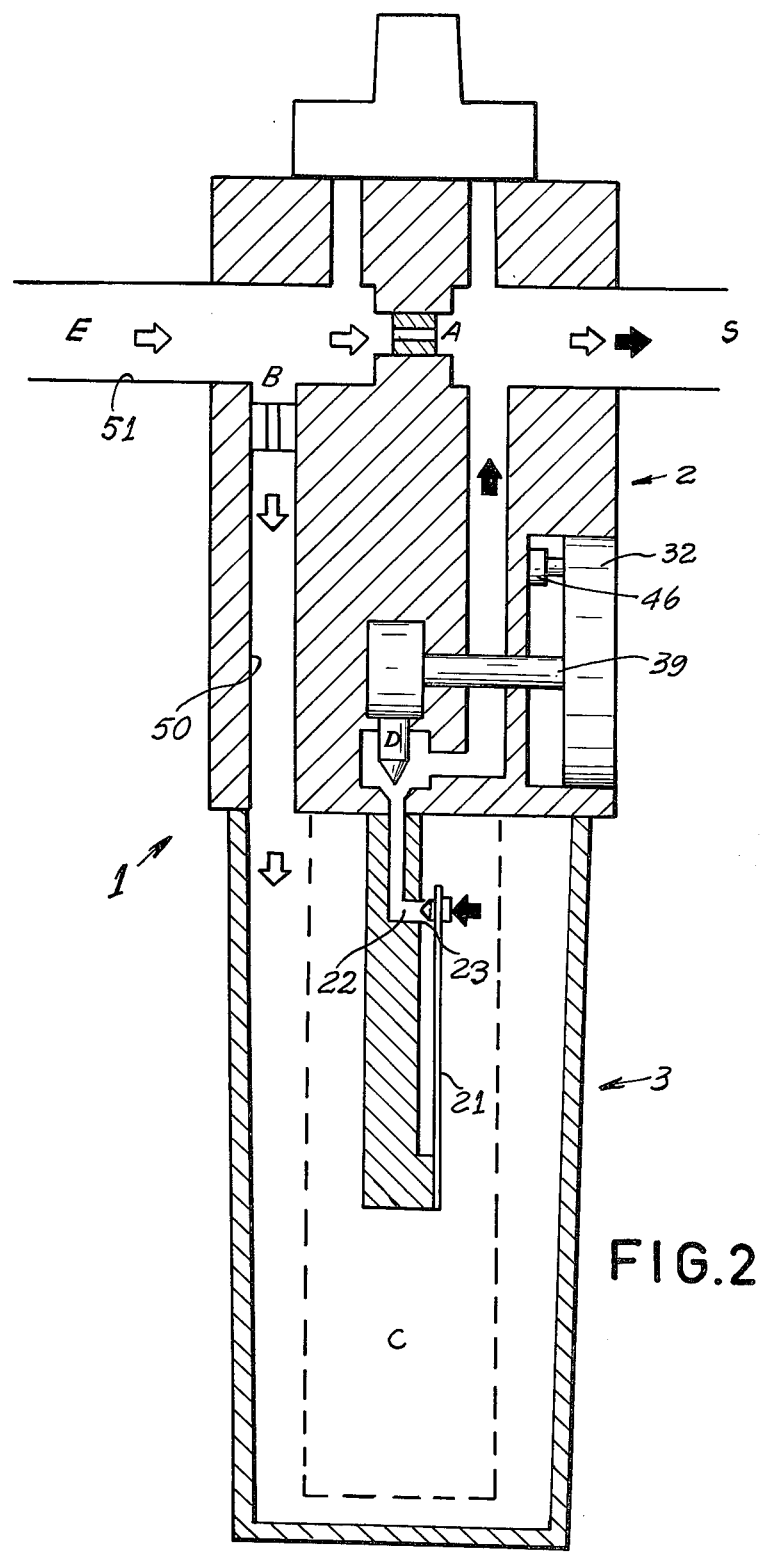
FIG. 2 shows a diagrammatic vertical section of the vaporizer of FIG. 1.

In accordance with FIGS. 1 and 2, the vaporizing device of this invention is of the kind in which the oxygen or vaporizing vehicle fueled through inlet E is branched into first and second streams, the first one going directly to the outlet S through a gauged bore A to create a differential pressure, and the second one being diverted, via gauged bore B, to the vaporization chamber C where it is mixed and saturated with the anesthetic liquid compound. The saturated carrier gas is returned through the needle valve D to join the said first stream to reach the outlet in a given concentration.

The structural improvements of this invention include the provision of a prismatic vertical body 1 composed by an upper and lower sections 2 and 3, the head or upper section 2 having detachable side wall 4,5 (FIG. 3), from which two opposite tubular members 6, 7 project horizontally, for the connection of the oxygen feeding tube and the vaporized anesthetic compound distribution, respectively.

Section 3 is a hollow body defining the vaporization chamber 8 encasing the vaporizing unit and the anesthetic liquid composition L. It is also provided with a front prismatic projection 9 having a level gauge 10 for indicating the liquid charge in the said chamber 8, and communicating passageways 11, 12 (FIG. 12) for the admission and draining respectively of the anesthetic liquid composition L.

As shown in FIGS. 1 and 2, liquid is stored in the hopperlike entrance section 13, its flow into the chamber being controlled by means of the regulating unit 14. Liquid may be drained off and removed by the regulating unit 16 of a known type, by positive pressure on the passageway 12.

A first improvement of this invention is the provision of the gauged bore A to regulate the main stream flow E of the vaporizing carrier, directly reaching the outlet S, and the identical gauged bore B, positioned within the downwardly directed branch of the oxygen tube, whose function is to keep constant the concentration of the emerging anesthetic mixture.

Each of the said A and B regulating units include a choke member 17, threaded in the internal wall of the fluid channel, and having an axial outlet bore 18 and two or more radial entrances 19, the entrance depending on the number and direction of the converging ducts. All of the said entrances discharge the anesthetic liquid into a central chamber 19' whose capacity is controlled and regulated by the adjustable tapered stud 20, which is externally driven across the said central chamber by a screwing action.

Figure 3:
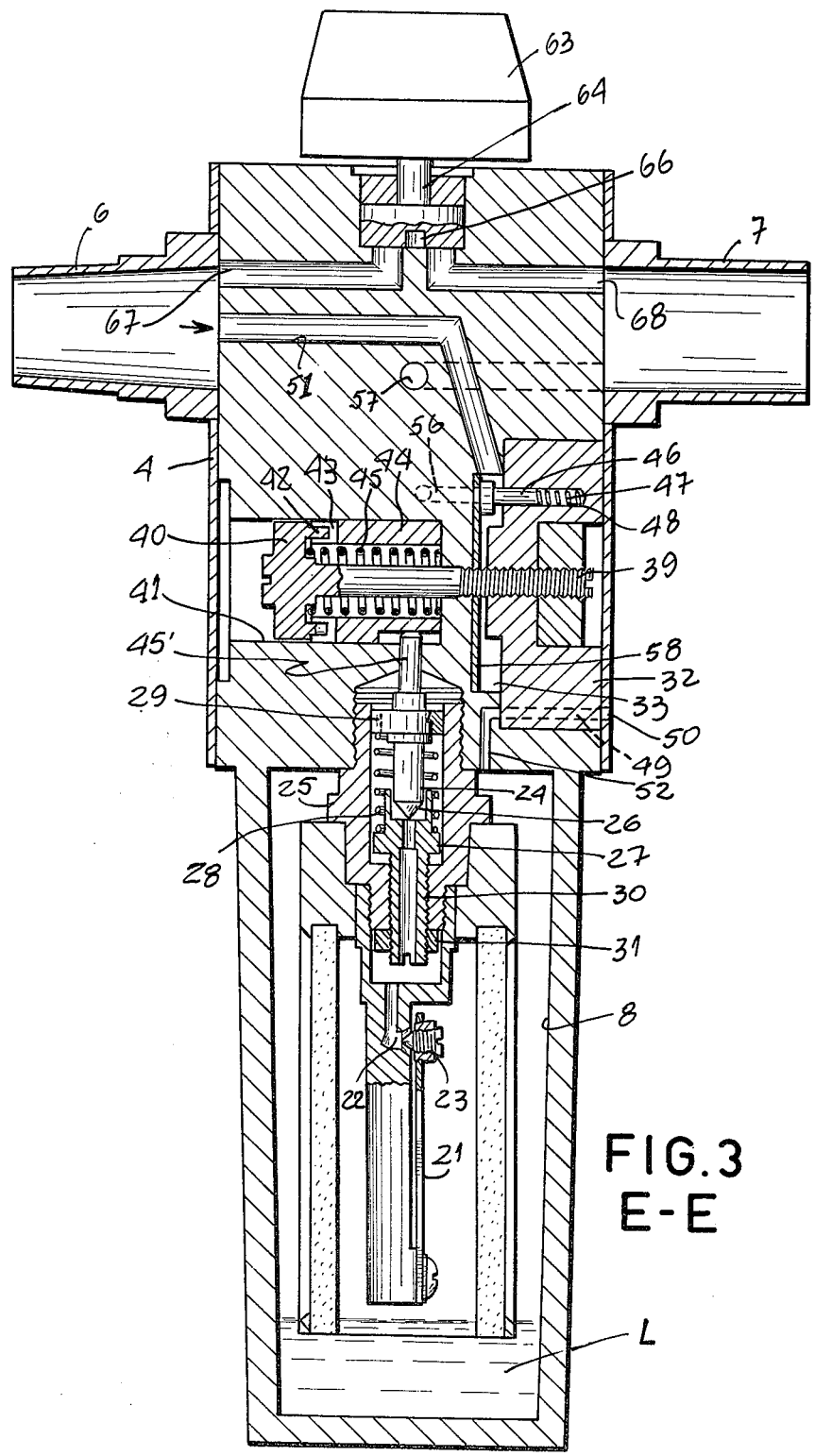
FIG. 3 shows a vertical section view of the same device, along line EE of FIG. 1.

FIGS. 2 and 3 illustrate improvements of the usual bi-metallic valve employed to regulate the outflow of vaporized liquid from the storage tank to the outlet S, through the needle valve to compensate for the undesired influence of temperature on the concentration ratio of the anesthetic composition. The improvements include utilizing a tapered adjustable stud 23 located on the free end of the bi-metallic valve plate 21, which may be driven into the entrance bore 22 of the interconnecting passageway leading to the needle-valve D.

This invention also includes improvements in the needle valve D itself (FIG. 3) which generally include a needle-pointed plunger 24 axially slidable in the cavity of a fixed sleeve 25 which is screwed into the upper section 2 of the vaporizing device and projects into the atomizing chamber 8 of the lower section 3 thereof.

The plunger 24 is supported by a coiled spring 28 whose upper end is secured to the flanged section 29 of the plunger 24 and to the flanged section of the valve seat body 27, into which slides the plunger to shut off the atomized anesthetic stream by the sealing action of its needle-point 26.

The improvement is provided by the downward projecting threaded tubular neck 30, extending axially from the valve seat body 27 through the lower portion of fixed sleeve 25 and emerging therefrom to be clasped by a nut 31.

It will be seen that by the cited construction, an exact determination of the shut-off position of the plunger 24 is attained, preventing any damage to its needle-point 26 due to excessively hard contact with the valve seat 27. This is accomplished by pushing the plunger 24 to its limit working position and then lifting the valve seat body 27 by means of the external nut 31 until a positive contact is established with the needle-point 26.

A further improvement of the vaporizer of this invention is found in the actuating and driving mechanisms of the needle-valve D which includes a rotary drum 32 (FIG. 3) housed in the circular recess 33 located in the upper or head section 2 of the vaporizer 1, said drum 32 being actuated by a lever-arm 34 (FIG. 4), which is tangentially projected therefrom emerging from the vertical slot 35 situated along the arcuate front side 36 of the head section 2. The arm 34 is provided with an index-knob 37 correlated to a linear scale 38 marked on the said front side 36.

The rotary drum 32 is supported on the axle 39 whose opposite end is formed into an enlarged circular piston section 40 provided with internally projecting pins 42 which fit into matching slots 43 on the top of a cam-sleeve 44, into which cylindrical cavity is placed a helicoidal spring 45, encircling the said crossing axle 39. The spring 45 acts to urge the piston section 40 and, therefore, its projecting axle 39, along the cylindrical chamber 41 horizontally placed into the said upper section 2 and opening in the lateral side thereof opposite to the casing 33.

The cam-sleeve 44 is positioned to be operatively abutting against the upper end of the radial actuator 45' of the needle 24 of the main shut-off valve set.

It can be seen that the actuating mechanism of the needle-valve 24 includes the angulaar manual displacement of the lever-arm 34 rotating the drum 32 and the axle 39 of the piston 40 which, by means of the pins and slots combination, causes rotation of the camsleeve 44 acting on the actuator 45' and thus driving forward or rearward the said plunger 24 in respect of the valve seat 27. angular Of course, the external scale 38 will permit a quick and precise reading at a glance, of the position of the needle-valve D in terms of volume of atomized anesthetic liquid compound flowing therethrough.

Figure 4:
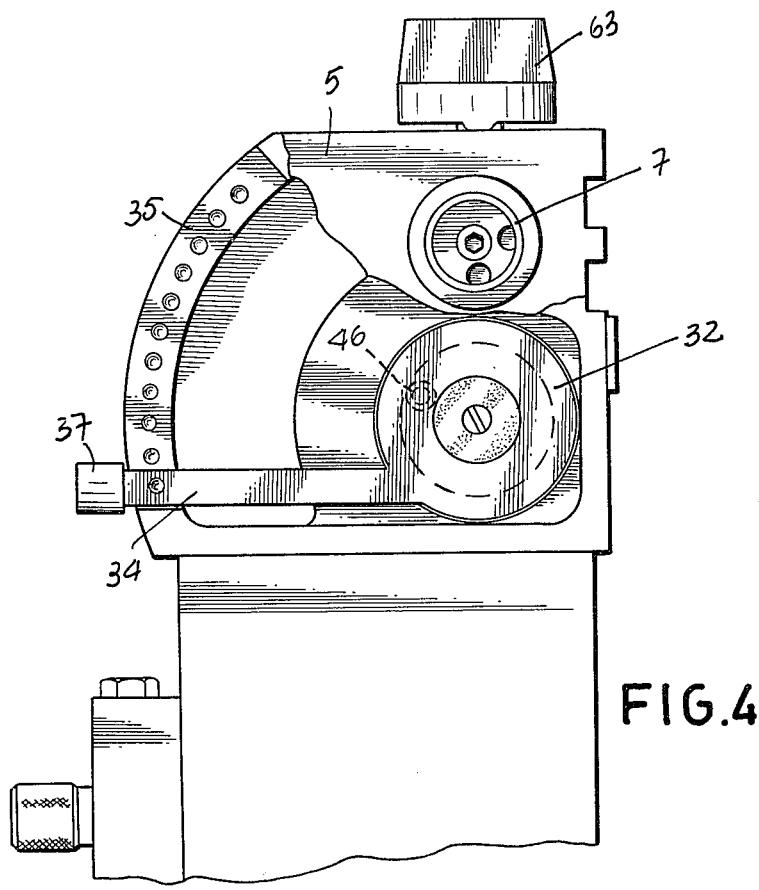
FIGS. 4 and 5 are lateral partially sectioned views of the outlet side of the device of FIG. 1.
Figure 5:
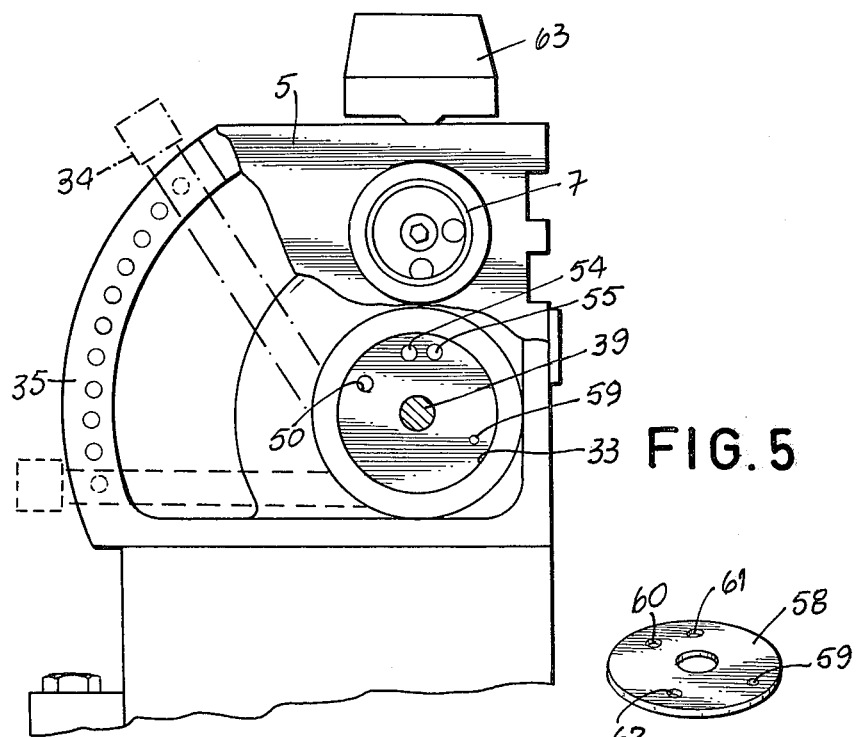

With further reference to the rotary drum 32, it is provided with a sealing stud 46 supported on the spring 47 (see FIGS. 3, 4 and 5). The stud 46 is encased into the recess 48 of the drum. The drum has a passageway 49 whose relative position is such that the "zero" index position of the lever-arm 34 (FIG. 1), i.e., the full closed position of the needle-valve D, the sealing stud 46 closes the branch 50 of the oxygen duct 51 (FIG. 9), thus preventing the vaporizing gas carrier from reaching the atomizing chamber 8. The transverse passageway 49 connects the vent pipe 52 with the vent port 53 opening in the lateral plate 5 of head section 2.

Under non-operative condition of the needle-valve actuating mechanism, with its driving arm 34 at the "zero" index scale position, no fresh oxygen will flow into the atomizing chamber 8 and no atomized mixture shall leave it due to the simultaneous closure of the needle-valve D and of the inlet duct 50 while the venting system 52, 49, 53 will allow the escape of the vapors generated by the self volatilization of the anesthetic liquid L contained in the storage tank 8, thus relieving the vapor pressure thereinto.

Figure 10:
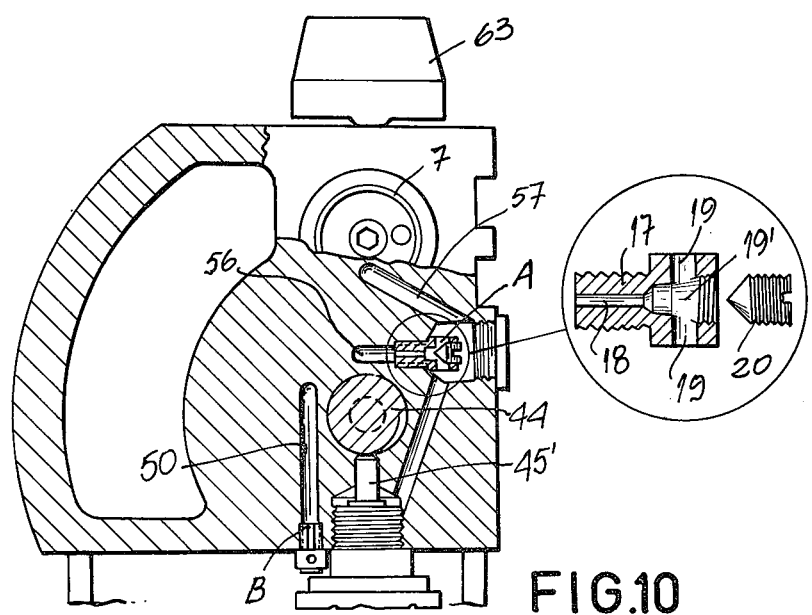
FIG. 10 is a partial view of the head part of the vaporizer detailing the gauged outlet bore.

In order to make the improved vaporizer of this invention useful for all kinds of anesthetic liquid compounds heretofore known, including those which require special care in closing or opening the oxygen inlet pipe, a further improvement is set forth wherein a receiving recess 33 is provided for the rotary drum to which the main oxygen inlet channel 51 discharges and from which extends the atomizing chamber 8 leading branch channel 50 as well as two other horizontally aligned and spaced ducts 54, 55. The first duct 54 is spaced apart from the said branch channel 50 an angular distance equal to the path of the lever-arm 34. Both of these ducts lead lead to the horizontal duct 56 (FIG. 10) which is a section of the path of the direct flow E-S system constituted by the inlet duct 51 and the outlet duct 57.

Figure 6:
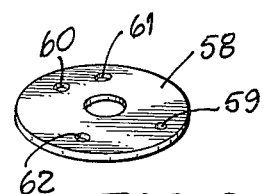
FIG. 6 is an enlarged perspective view of the main control plate of the driving mechanism.

Abutted against the bottom side of the circular recess 33 a circular plate 58 is provided (FIG. 6) which is drilled with a series of holes 61, 60 and 62 so disposed to match with the openings of the ducts 55, 54 and 50 respectively. The plate also includes a positioning hole 59.

Figure 7:
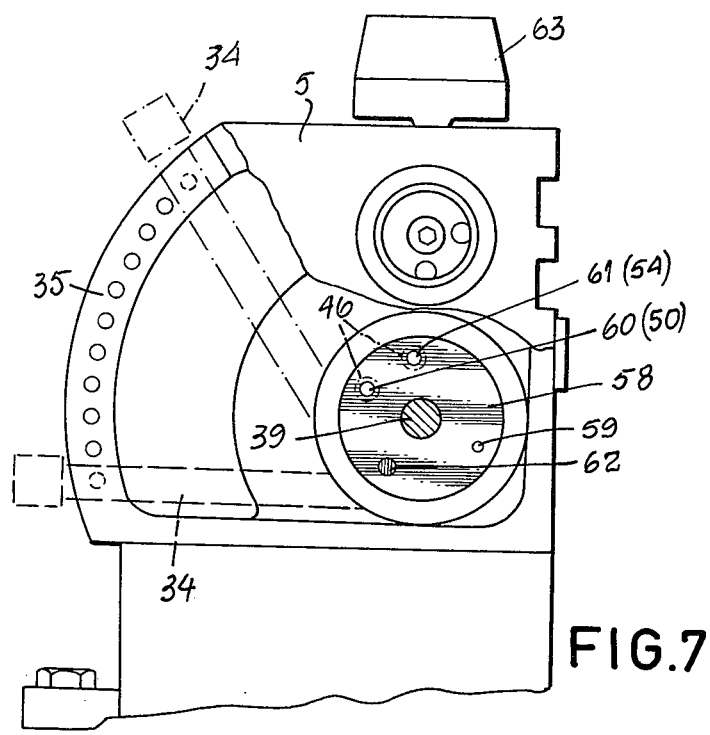
FIGS. 7 and 8 show two different operating positions of the said mechanism.

This plate 58 will be differently positioned in accordance with the nature of the anesthetic liquid composition. For instance, in case of use of anesthetic compound which allows the full closing of the direct path flow D-S and, consequently, the integral flow to the atomizing chamber 8, the said plate 58 will be placed as shown in FIG. 7, that means, with the hole 60 matching the opening of the branch duct 50 and 61 matching with the opening of the duct 54, while the other hole 55 will be sealed by the plate wall.

Under these conditions, by turning the rotary drum 32, the sealing stud 46 will travel from a first limit position (closing both the hole 60 and the duct 50) to a second limit position shutting off the hole 61 and passageway 54, passing by intermediary positions in which both passageways 50 and 54 are open.

Figure 8:
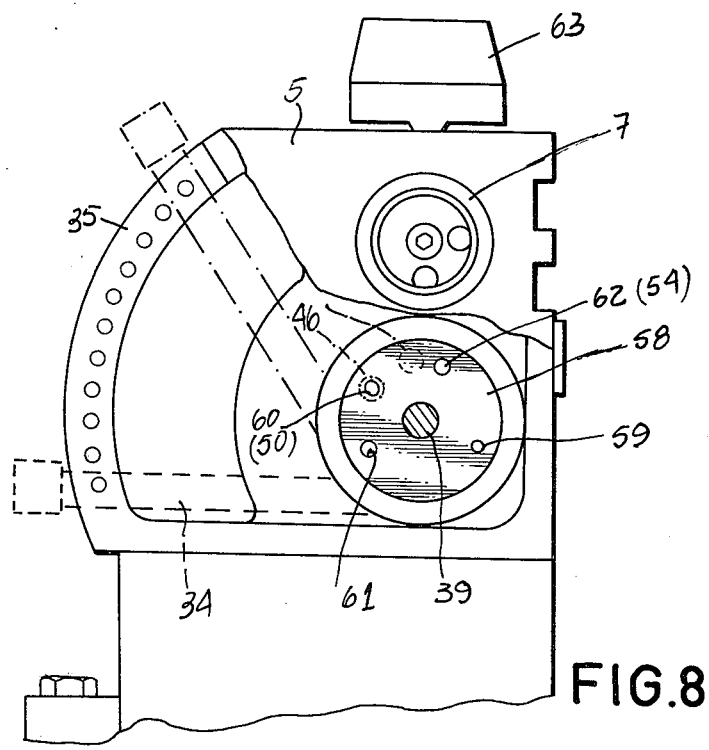

When an anesthetic liquid composition is used which does not necessitate fully closing the direct-flow path, D-S, the said plate 58 is mounted as shown in FIG. 8, i.e., turned 180° in respect to the formerly disclosed position.

A final aspect of this invention is embodied in the presence of a free-flow valve interconnected in an inlet-outlet oxygen flow system 67, 68 (FIG. 9) in which the said valve includes a driving knob 63 located on the top of the vaporizer 1, applied to the end of a shaft 64 provided with a cylindrical enlargement 65, rotatively encased into the recess 64′, having, on its lower end, a diametral slot 66 acting as an interconnecting duct section for the said inlet and outlet passageways 67, 68.

Figure 9:
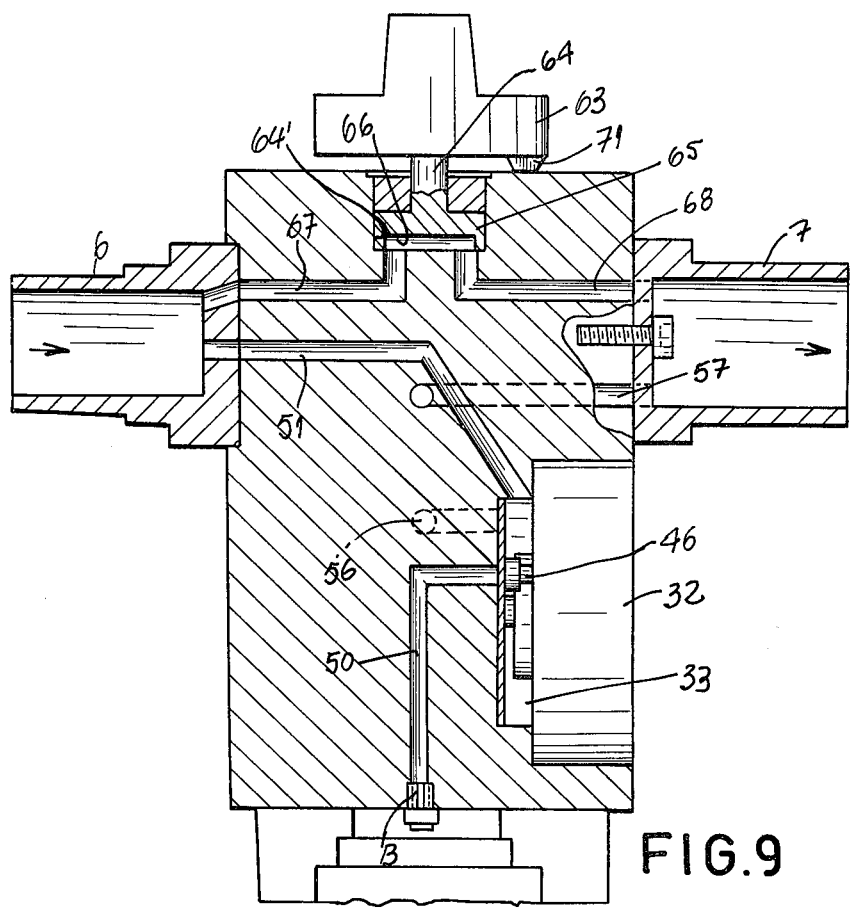
FIG. 9 is a schematic view of the said vaporizer showing the same in unoperative or idle position.

To turn the vaporizer on, the said knob 63 is in the position as shown in FIG. 3, interrupting the passage of the oxygen through the said free-flow system, thus allowing the vaporizing gas carrier to pass through the duct 51. To turn it in the off position, the knob 63 is placed as illustrated in FIG. 9, in which the pipe system 67, 68 allows the flow of the oxygen into the direct path 6–7.

This free-flow system 67, 66, 68 is particularly important and useful in cases of gang-unit arrangements (FIG. 13) forming a battery of vaporizers 1. To do that, the lateral plates 4, 5 of the intermediary units shall be removed. In this arrangement, the vapaorizer being used shall be turned on, while the others shall be left in the off position. All the units placed before the one turned on have their needle-valve in the off position, establishing thus a direct free-flow passage for the oxygen, while the units placed after the one in use, will have a free-flow for the anesthetic mixture.

To avoid the accidental opening of the needle-valve in the idle units collectively arranged, the lever arm 34 is equipped with a safety device (FIG. 11) constituting the horizontal bar 69 laterally and upperly contacted by the stud 70 driven by the lower rib 71 of the knob 63. The bar 69, in the idle position of the needle-valve, fits into the recess 6 provided in the upper enlarged end 72 of a spring 74 supported vertical rod 73, whose lower end fits into the recess 75 located in the lateral side of the rotary drum 32.

This way, when the knob 63 is in the off i.e., zero index, position (FIG. 9), the rib 71 will push the bar 69 downward thus forcing the rod 73 to slide down engaging the recess 75 to lock the drum 32. Otherwise, the spring 74 compresses under the sliding movement of the rod head 72 until the movement in which the said drum is turned in the locking position.

What I claim is:

1. A vaporizing device useful for the carrying of liquid anesthesia by a carrier gas matrix, said device of the type utilizing two separate streams of carrier gas with the first of said streams not immediately contacting said liquid and the second of said streams contacting and carrying said liquid within said stream to a final mixing chamber in which said second stream is reunited and mixed with said first stream and the control of the amount of each of the streams helps to determine the amount of liquid anesthesia provided to the patient, the device comprising:

a. a body shaped to allow for abutment at the sides of said body by another said device, said body including removable side panels, an upper section and a lower section;

b. said lower section of said body defining a chamber for contacting mixing said anesthetic liquid with said second stream, said lower section including means for introduction of said liquid into said chamber, and a second conduit means including valve means for the introduction of said second stream;

c. other conduit means for carrying said anesthetic enriched second stream into said final mixing chamber, said means including a conduit which interconnects said chambers and separate valve means for controlling the amount of said enriched second stream entering said final chamber;

d. said upper section including first stream conduit means for carrying said first stream to said final mixing chamber including a valve means for controlling the amount of said first stream entering said chamber.

2. The device of claim 1 in which said valve means in said first stream conduit and said second stream conduit are identical and comprise a choke member with an internally threaded socket depending from the interior wall of the conduit, said choke member having bores therethrough correponding to and in alignment with the conduit, and a screw means for engaging said socket thereby controlling the flow of said stream.

3. The device of claim 1 in which bimetallic valve and a needle-valve is utilized as part of said separate valve means, a passageway connects said valves and said bimetallic valve controls the flow from said first chamber to said needle-valve, said bimetallic valve comprising a tapered threaded adjustable stud which adjustably penetrates said passageway.

4. The device of claim 1 in which said needle-valve comprises a threaded adjustable valve seat to minimize wear on the valve parts.

5. The device of claim 3 in which the needle-valve is activated by a rotatable cam sleeve rotatably connected to an external actuating means, said actuating means directly correlated with an external scale.

6. The device of claim 3 in which said valve means include a venting means which is rendered operative to discharge the residue of the enriched second stream left in said valve means after said needle-valve has been closed.

7. The device of claim 5 in which locking means are provided for said external actuating means.

8. The device of claim 1 in which said first stream can be directly controllable connected to another identical device.

\* \* \* \* \*